US005512200A

United States Patent [19]
Garcia

[11] Patent Number: 5,512,200
[45] Date of Patent: Apr. 30, 1996

[54] LOW PH ACIDIC COMPOSITIONS

[75] Inventor: Silverio M. Garcia, Spring, Tex.

[73] Assignee: Thomas G. Bongard, Jupiter, Fla.

[21] Appl. No.: 229,373

[22] Filed: Apr. 18, 1994

[51] Int. Cl.⁶ ..................................................... A61K 33/00
[52] U.S. Cl. ................. 252/142; 134/3; 134/28; 252/79.3; 252/86; 252/87; 252/136; 252/173; 252/174.19; 252/178; 252/180; 252/181; 252/DIG. 10; 514/844; 514/859; 514/861; 514/858; 514/865
[58] Field of Search ..................................... 514/844, 859, 514/861, 865, 858; 252/142, 79.3, 86, 87, 136, 173, 174.19, 178, 180, 181, DIG. 10; 134/3, 28

[56] References Cited

U.S. PATENT DOCUMENTS

| | | | |
|---|---|---|---|
| 4,447,364 | 10/1984 | Garcia | 252/142 |
| 4,459,202 | 10/1984 | Garcia | 252/364 |
| 4,483,887 | 11/1984 | Garcia | 427/436 |
| 4,675,120 | 6/1987 | Martucci | 252/8.552 |
| 4,970,014 | 11/1990 | Garcia | 252/79.3 |
| 4,970,015 | 11/1990 | Garcia | 252/79.4 |
| 5,019,288 | 5/1991 | Garcia | 252/79.2 |

OTHER PUBLICATIONS

The Merck Index, an Encyclopedia of Chemicals and Drugs, Ninth Edition, Martha Windholz et al, Editors, Published by Merck & Co., Inc., Rahway, N.J., 1976, pp. 1101–1102, item 8261.

*Primary Examiner*—Ronald W. Griffin
*Attorney, Agent, or Firm*—Quarles & Brady

[57] ABSTRACT

Low pH acidic compositions for uses related generally to chemical, pharmaceutical and cosmetic agents and more particularly, but not limited to, used as bactericides, fungicides, germicides and virucides; all having pH values of less than about 2.0 in their final form. These low pH acidic compositions generally comprise two phases in solution. Phase I comprises from about 2 to about 98 weight percent of varying percentages of several chemical, pharmaceutical and cosmetic substances.

Phase II comprises from about 2 to about 99 weight percent of an active aqueous acidic component having a pH value of less than about 1. This phase II aqueous acidic component is produced by:

(a) admixing from about 5 to about 20 weight percent of a strong acid that has a high degree of dissociation with from about 5 to about 20 weight percent of another strong acid with a lower degree of dissociation, but still classified as strong, in a suitable vessel for an effective period of time to produce a substantially homogeneous acidic mixture; and b) admixing from about 1 to about 5 weight percent of weaker acids with low degrees of dissociation taken from the families of the hydroxycarboxylic acids or alpha hydroxy acids and from about 1 to about 5 weight percent of a dicarboxylic acid with the aqueous acidic mixture in an effective amount of water to provide an aqueous acidic mixture.

6 Claims, No Drawings

LOW PH ACIDIC COMPOSITIONS

BACKGROUND OF THE INVENTION

The present invention involves the use of an aqueous acidic composition as the principal, or core, component of a number of compositions including, but not limited to, metal cleaners, anti-oxidants and de-greasers, cleaners for glass, porcelain and other ceramics, metal plating baths, sterilants and bacteriostatic agents for liquids including water treatment, cosmetics, soaps and detergents, topical antiseptics, eye and ear drops, and pharmaceutical agents, and the use of those compositions. More particularly, the present invention relates to an improved, four acid core component and its formulation with other ingredients and use for these various purposes.

Although now well known in the patent literature, there is still much to be clarified about the manner in which low pH, non-toxic aqueous compositions function to achieve their intended result without causing the caustic burns and other damage caused by strong acids. So far as is known, the first disclosure of such compositions in the patent literature is set out in U.S. Pat. No. 4,459,202 (Garcia), which utilized an acidic solvent composition including two strong and two weak acids for recovering bituminous products from tar sands. The specification of that patent notes that the composition is non-corrosive and not a health hazard. Shortly after the issuance of that patent, U.S. Pat. Nos. 4,477,364 and 4,483,887 (again, Garcia was the inventor) issued describing the use of that same four acid composition as a component of a glass cleaner and metal plating substrate, respectively, each of which was described as being substantially non-toxic and inert to the human skin.

Since those 1984 patents, several other patents have issued describing the use of this four acid composition as a core component in other compositions, including U.S. Pat. Nos. 4,675,120 (Martucci), 4,970,014 (Garcia), 4,970,015 (Garcia) and 5,019,288 (Garcia) for well acidizing, tertiary oil recovery, removing rust from metal, cleaning aluminum, radiator cleaning, boiler and heat exchanger cleaning, and copper cleaning. Canadian (No. 1,231,053 (Garcia)) and Mexican (No. 158,149 (Garcia)), also issued (in 1988 and 1989, respectively) which are directed to the four acid composition.

To the extent that the function of this four acid core component is understood, that function is described in those issued patents, each of which is incorporated herein in their entireties by this specific reference thereto. Briefly, the combination of first and second strong acids with third and fourth, weaker acids has the effect of forcing the weaker acids to act as conjugate bases for the strong acids to accept (in the terminology of the Bronsted-Lowry theory for describing the behavior of acids and bases in aqueous solution) hydrogen ions (actually hydronium ions $H_3O^+$ when in aqueous solution) from the strong acids. In this manner, acid solutions with extremely low pH values and high amounts of free hydrogen ions are made. These solutions are non-corrosive to metal, innocuous to skin and capable of providing enormous amounts of hydrogen ions that, when combined with other acids, provide an excellent environment for effective performance as bacteriastats and cleaning, disinfecting and preparation of all kinds of surfaces by creating a protective mantle that does not allow any type of micro-organism to live in such a low pH environment.

Despite the rather remarkable behavior of this four acid core component disclosed in the above-incorporated patents in water and the many uses for which it is capable of being adapted, it is characterized by several shortcomings when used in certain applications. For instance, in studies conducted with a disinfectant formulated from the four component composition for topical application to the skin, the disinfectant caused a reddening of the skin and a burning sensation at concentrations high enough to insure adequate disinfection. Likewise, when formulated into plating and cleaning solutions and the like such as are contemplated by the above-incorporated patents, the result is a plating or cleaning solution which, when it contacts the skin, has a similar result such that it is desirable to re-formulate these solutions in a manner which does not decrease their efficacy but which is safer for the person(s) using the solution to handle.

It is, therefore, a primary object of this invention to provide a core composition capable of being formulated into a variety of different solutions for use in water treatment; cleaning; cleaning, plating, and/or re-finishing metals; disinfecting; pharmaceuticals; and cosmetics.

It is another object of the present invention to provide methods for the use of the different solutions formulated with the core composition of the present invention.

These, and other, objects of the present invention will be made clear by the following description of the presently preferred embodiments thereof.

SUMMARY OF THE INVENTION

These objects are achieved by providing a composition having a low pH which is comprised of first and second strong acids, the first acid being an inorganic acid which dissociates essentially completely in water and the second acid likewise being an inorganic acid but not as strong as the first acid, preferably with a dissociation constant of less than about $10^{-1}$, mixed with third and fourth acids, both the third and fourth acids being organic acids, the third having a dissociation constant of between about $10^{-1}$ and about $10^{-5}$ and the fourth having a dissociation constant of about $10^{-4}$ or less. This four acid composition is used as a core component in a number of aqueous solutions which are used for a wide variety of purposes, including water treatment, preservatives, pharmaceuticals, cleansers, disinfectants, metal cleaning, brightening and plating agents, battery acid fluids, and cosmetic agents, and more particularly with regard to pharmaceutical agents, but not limited to, antimicrobials, bactericides, fungicides, sporocides and virucides.

DETAILED DESCRIPTION OF THE PREFERRED EMBODIMENTS

The present invention relates to a four acid core composition having very low pH and the formulation of that core composition into low pH acidic compositions. The four acids comprising that core composition include first and second inorganic acids and third and fourth organic acids, each being mixed with each other in acid-base conjugate pairs before they are mixed with each other to form the four acid core composition.

The first acid is an inorganic acid which dissociates essentially completely in water, i.e., is a strong acid. Prior low pH compositions such as those described in the several above-incorporated patents describe the use of hydrochloric acid as the first acid, but other inorganic, strong acids may likewise be used to advantage in connection with the present invention, including hydrobromic, sulfuric, nitric, chloric, perchloric, permanganic, and hydroiodic acids. In a particularly preferred embodiment of the present invention, this first acid is hydrobromic acid. The first acid comprises between about 5 and about 20 weight per cent of the final concentration of the four acid core composition, and preferably between about 5% and about 12%.

The first acid is mixed with the second, also inorganic acid, resulting in a conjugate acid-base pair in which the second acid, being a weaker acid, effectively functions as a base to accept hydrogen ions ($H^+$) from the first acid. This second acid is selected from the group of inorganic acids having a dissociation constant of less than about $10^{-1}$, including, but not limited to, chlorous, hydrazoic, hydrofluoric, hydrosulfuric, hydrosulfurous, hypobromous, hypochlorous, hypophosphorous, iodic, nitrous, periodic, phosphoric, phosphorous, pyrophosphoric, and sulfurous acids. In a particularly preferred embodiment, the second acid is phosphoric acid, and comprises between about 5 and about 20 weight percent of the four acid core composition, and preferably between about 5 and about 12%.

The third acid is an organic acid selected from the group consisting of those organic acids having a dissociation constant of from about $10^{-1}$ to about $10^{-5}$, and the fourth acid is likewise an organic acid, but is selected from the group of organic acids having a dissociation constant of less than about $10^{-4}$. Preferred third and fourth acids are hydroxy- and alphahydroxycarboxylic acids and dicarboxylic acids selected in pairs so as to serve as acid-base conjugates so that the weaker acid effectively functions as the base of the conjugate pair, and may be either aliphatic or aromatic acids. Suitable third acids include, but not limited to, fumaric, maleic, malonic, oxalic, phthalic, salicylic and tartaric acids, and fourth acids which may be used to advantage in connection with the composition of the present invention include, but are not limited to acetic, acrylic, adipic, benzoic, butyric, carbonic, citric, diethylmalonic, di-n-propylmalonic, glutaric, glycolic, hydroxybenzoic, hydroxybutyric, hydroxymethyl- and other substituted benzoic acids, isobutyric, isocitric, isovaleric, lactic, malic, mandelic, methylethylmalonic, methylmalonic, phenylacetic, pimelic, propionic, pyrotartaric, suberic, succinic, and valeric acids. Those skilled in the art will recognize from this disclosure that other, longer chain aliphatic and aromatic carboxylic, dicarboxylic, hydroxycarboxylic and substituted carboxylic acids may also be used to advantage such that the lists set out herein are not inclusive of those third and fourth acids suitable for use in connection with the composition of the present invention. Those skilled in the art who have the benefit of this disclosure will also recognize that the grouping of these organic acids into third and fourth acids is not necessarily exhaustive of the pairings of acids as third and fourth acids. Satisfactory results can, for instance, be achieved by selecting an organic acid such as citric or malic acid, both having dissociation constants of about $10^{-4}$, and using them in combination with a weaker acid such as succinic or glutaric acids, both having dissociation constants of about $10^{-5}$. In particular, it has been found that the combination of a hydroxy-carboxylic acid (particularly an α-hydroxycarboxylic acid) and a dicarboxylic acid gives satisfactory results, and those skilled in the art who have the benefit of this disclosure will recognize that hydroxycarboxylic and dicarboxylic acids may be included in either or both of the groups of organic acids set out above. In general, however, it is preferred to use a combination of third and fourth acids in which the dissociation constant of the third acid is in the range of from about $10^{-1}$ to about $10^{-3}$ and a fourth acid having a dissociation constant of less than about $10^{-4}$, hence the grouping of the acids as set out above.

The four acid core composition is prepared by mixing the first and second acids in a first container and mixing the third and fourth acids in water in a separate, second container. The two acidic mixtures are then used as stock solutions for mixing with each other to form the four acid aqueous core composition, preferably having a pH of less than 1. The resulting aqueous core composition is then used as a component for a number of aqueous formulations for the several purposes listed above, the particular ingredients of each such formulation being determined by the particular use contemplated.

For instance, low pH acidic pharmaceutical agents are made from this four acid core composition which are useful in the topical treatment of infections caused by bacterial, viral, and fungal agents, for use as a cold sterilant or an active disinfecting ingredient in cleaning solutions for personal, commercial, and domestic uses, and also for use in cosmetic compounds to help alleviate a diverse number of skin disorders. These pharmaceutical agents, sterilants, disinfectants, and cosmetics are blended in two basic phases, the first phase comprising agents such as those that provide added protection to tissue and membranes, serve as vehicles for carrying the active ingredients, and give texture to the resulting final solutions, and some of which are also active ingredients in their own right for the specific use that the given formulation is intended. These pharmaceutical chemicals generally comprise from about 1 to about 99 weight percent of the resolution final solutions. The percentages of these components varies depending on the purpose of the final solutions. Substances such as, but not limited to, moisturizers, surfactants, emollients, humectants, cetyl alcohol, stearyl alcohol, witch hazel, skin bleaching agents, detergents and soaps, rose water, lemon juice, water-based scents and colorants, topical anesthetics, corticosteroid-based creams, undecylenic acid, propylene glycol, hyaluronic acid, glycerin, glycerol, boric acid, salicylic acid, sodium hypochlorate, sorbic acid, silicone, vitamin E acetate, pramoxine HCL, AQUAPALM (Hoffman-LaRoche, Inc.), DERMABASE (Borden, Inc.), emulsifiers and wetting agents such as those sold under the trademark BRIJ (ICI U.S., Inc.), allantoin, and aloe vera are used. The second phase is the aqueous acidic composition, which is the active ingredient of the resulting final solution, and which comprises from about 1 to about 99 weight percent of the final solution.

Such low pH pharmaceutical agents have broad applications in the topical treatment of infections in human and animal tissue, whether caused by bacteria, virus, or fungus. These low pH formulations may also include alpha-hydroxy acids (fruit acids) for the treatment of minor skin disorders such as rashes, wrinkles, dry skin, acne, age spots, and ichthyosis, and even in the treatment of certain skin cancers.

These low pH pharmaceutical agents function to create a very low pH environment and to maintain that low pH environment for a long enough period of time to rupture the cell wall (in the case of bacterial and fungal agents) or break down the envelope (in the case of viral agents) or to keep these infectious agents from reproducing/replicating, thereby reducing their count and allowing the body's immune system to heal the body. The involvement of the immune system, coupled with the ability of the composition of the present invention to reduce the population of the immunogenic microbial agent, suggests the formulation of the composition together with various peptides such as protein A, interferon, interleukins and other such immunostimulants and/or modulators of immune system function, for treatment of infection. In such formulations, and depending upon the particular peptide being utilized, it may be necessary to provide a pharmacological base which protects the peptide against the low pH of the core composition, to buffer the combination so as to prevent such effects, or to protect the peptide by, for instance, microencapsulation, all as known in the art. The combination may likewise include any of several adjuvants known in the art.

Without a pharmaceutical base, these low pH solutions may not exhibit long enough retention time on the tissue to allow effective action against these infectious agents. It is for the purposes of extending retention time, giving the solution a more pleasant texture and color, and masking any associated odors that these additional components are used.

In a second use of the four acid core composition, the core composition is formulated for use in water treatment with trace minerals and metals such as copper which allow the formulations to disperse in large bodies of water evenly with concentrations at the surface mirroring concentrations at the bottom. In the past, treatments with products such as copper sulfate pentahydrate were broadcast directly on the surface of small and large bodies of water, canals and streams with the resulting concentrations being weaker at the surface while reaching toxic levels at the bottom. The incorporation of the core composition of the present invention into a formulation including copper sulfate, trace minerals, and/or metal salts, however, allows for more predictable treatment levels and lower overall treatment concentrations, the result being a more ecologically safe water treatment for fish and beneficial aquatic life. In such formulations, it is generally preferred that the four acid core composition comprise between about 70 and about 95% (by weight) of the formulation, the remainder being the metal in soluble form, e.g., copper sulfate pentahydrate. Formulations are prepared both for treatment of the drinking water supply and for sewage and/or effluent treatment, and may also include chlorine, fluoride, flocculating agents, and such other components as are known in the water treatment art.

In another use of the core composition, strong acids such as sulfuric, hydrofluoric, phosphoric, hydrochloric, and/or hydrobromic, or mixtures of such acids, are added for preparation of aqueous solutions used for cleaning, oxide removal, carbonate removal, brightening, and pickling of glass, aluminum, copper, and other metals, and ceramics. For instance, addition of hydrofluoric acid in ratios ranging from about 1 part to 2 parts (by weight or volume) of the core composition up to about 1 part to 40 parts hydrofluoric acid results in a composition for cleaning ceramics and glass and cleaning and removing oxides from aluminum. Addition of, for instance, a mixture of hydrochloric, hydrofluoric, phosphoric, and sulfuric acids in ratios of 20–40:5–15:5–15:20–30 parts (by weight or volume), respectively, to like amounts of the core composition results in a composition which is used for cleaning and pickling metals. An aqueous solution containing between about 3–7 parts hydrochloric acid to about 7–3 parts (by weight or volume) of the core composition is useful in removing oxide and carbonate deposits from the metal surfaces of cooling towers, evaporators, chillers, refrigeration and air conditioning equipment, radiators, and heat exchangers.

When about one up to about 5 parts of the core composition is combined with between about 0.5 to about 7.5 parts (by weight or volume) of an acid such as sulfuric acid, the resulting aqueous solution is used to advantage as a battery acid. Depending upon the type of battery, acids besides sulfuric are likewise used for the same purpose.

The present invention can be better understood by reference to the following examples of a presently preferred embodiment of the four acid core composition and several formulations including that core composition for use for different purposes. It will be recognized by those skilled in the art that these examples are illustrative of the invention, set out for the purposes of compliance with the requirements of the Patent Statute, and do not represent an exhaustive listing of all uses and possible formulations of the compositions of the present invention.

EXAMPLE I

Preparation of Aqueous Four Acid Core Composition 3.57 pounds of hydrochloric acid and 2.08 pounds of phosphoric acid were added to a container and the acids were stirred to produce a substantially homogeneous acidic mixture. During the mixing of the hydrochloric acid and the phosphoric acid fumes were generated. Thus, the mixing was carried out in a ventilated area. 16.6 pounds of water was then placed into a second container. 5.64 pounds of the hydrochloric-phosphoric mixture was added to the water in the second container. The resulting aqueous acidic solution was mixed thoroughly. Thereafter, 1.08 pounds of powdered citric acid and 0.75 pounds of powdered oxalic acid were admixed into the aqueous acidic mixture to produce an aqueous acidic composition.

The aqueous acidic composition was then diluted by admixing 24.07 pounds of the aqueous acidic composition with 16.6 pounds of water in a third container. The aqueous acidic composition and water were thoroughly stirred and provided approximately 4.85 gallons (40.7 pounds) of an aqueous acidic component having a pH value of about 0.49.

The mixing and storage containers employed were formed of materials substantially acid resistant. Further, all containers were covered for safety reasons and to prevent foreign materials from being injected into the aqueous acidic component.

EXAMPLE II

Preparation of Four Acidic Core Composition

A second embodiment of the four acid aqueous core composition was prepared by following the same method as is set out in Example I, above but replacing the hydrochloric acid with hydrobromic acid and substituting glutaric acid for oxalic acid.

EXAMPLE III

Preparation of a Pharmaceutical Agent

In order to make 100 kgs. of a pharmaceutical agent for use as ear drops formulated in accordance with the present invention, 50 kgs of propylene glycol, USP were blended together with 47 kgs. of glycerin, USP 99.5% and 100 grams of sorbic acid FCC. The solution was blended in a container of sufficient size until the propylene glycol, the glycerin and the sorbic acid are completely blended. To this blend, 2.9 kgs of the aqueous acidic core composition blended in Example II was added with agitation until the complete blend is thoroughly mixed, but no less than about 10 minutes.

EXAMPLE IV

Preparation of a Maleic Acid Core Composition

This acidic component was blended in the same manner as Example II above except that in place of the glutaric acid, maleic acid was used.

EXAMPLE V

Preparation of a Pharmaceutical Agent

To make 100 kgs. of an aloe vera-based acidic cream for use in treatment of sunburn, other minor burns, minor cuts and bites, and open sores such as decubitus ulcers, viral lesions, and infections, three distinct steps were taken. In the first step, 3.7 kgs of BRIJ 721 was blended in a properly jacketed vessel with 9.3 kgs of cetyl alcohol, 7.6 kgs of vitamin E acetate and 0.02 kgs of AQUAPALM. This blend was blended thoroughly and heated to 65° C. In the second step, 75.88 kgs of aloe vera gel was blended in a second jacketed vessel with 0.50 kgs of pramoxine HCl, blended thoroughly and heated to 65° C. With quick agitation, these two blends were admixed together for 10 to 15 minutes until a homogeneous emulsion is made. This emulsion was then allowed to cool with agitation to a temperature between 48° and 50° C. In a non-metallic container, 5 kgs. of the aqueous acidic composition of Example IV above was then admixed with the emulsion blended before and cooled while stirring until the temperature was less than 45° C.

EXAMPLE VI

Preparation of a Silicone-based Pharmaceutical Agent

In order to prepare 100 kgs of a silicone-based acidic pharmaceutical cream for use in treatment of fungal infections such as athlete's foot, three distinct steps were taken. The first step is to blend in a jacketed vessel 8 kgs. undecylenic acid, 6 kgs of BRIJ 621, 10 kgs. of stearyl alcohol and 7.6 kgs. of vitamin E acetate. This blend is mixed thoroughly and heated to between 65° and 75° C.

The second step is the thorough blending of 32.9 kgs. of water with 0.5 kgs of pramoxine HCl and again heating to between 65° and 75° C. Once these two steps have been reached, they are both blended together until the emulsion reached is uniform in nature. This emulsion is then cooled to between 60° and 75° C., at which point silicone R221 is added and blended into the emulsion. The resulting mixture is then allowed to cool to between 48° and 50° C. and transferred to a non-metallic vessel for further blending. To this blend, 15 kgs. of the aqueous acidic composition of Example II above is added and admixed until the cream sets and reaches a temperature of 35° C. or less.

EXAMPLE VII

Preparation of a Citric Acid-based Pharmaceutical Agent

In a suitable vessel, blend equal parts, by weight, of MINUTE MAID concentrated lemon juice and the core composition prepared in Example II above until a homogeneous blend has been achieved. Add to this blend equal amounts of witch hazel and rose water to give odor and texture, and to maintain the clear appearance, and the resulting solution is used as a wrinkle cream and for treating age spots.

EXAMPLE VIII

Preparation of Pharmaceutical Agent

The core composition made in accordance with Example IV, above was diluted with water to a 10% strength (by weight). The resulting aqueous pharmaceutical agent is used for treatment of eczema and other mild skin disorders. That same pharmaceutical agent is applied in a mist with a spray bottle to the skin of burn victims to prevent infection of the burn and promote healing.

EXAMPLE IX

Anti-microbial Activity of Four Acid Core Composition

The four acid core composition of the present invention was prepared in accordance with Example II, above and tested for activity against viruses in the following manner. The composition was tested at the concentrations set out in the following table. Each test was conducted by contacting suspensions of the respective virus with the listed concentration of the core composition at room temperature for 10 or 30 mins. as indicated. The table sets out the lowest concentration of the composition which gave 100% inactivation of the virus.

| VIRUS | Exposure Time | % of pH | Titer of Virus (PFU/ml) | % Inactivation |
|---|---|---|---|---|
| Poliovirus type 1 | 10 min. | 0 | $2.0 \times 10^5$ | 0 (UNTREATED CONTROL) |
| | 10 min. | 1.0% | 0 | 100% |
| | 30 min. | 0.1% | 0 | 100% |
| Herpes simplex virus type 1 | 10 min. | 0 | $2.0 \times 10^7$ | 0 (UNTREATED CONTROL) |
| | 10 min. | 0.1% | 0 | 100% |
| Herpes simplex virus type 2 | 10 min. | 0 | $2.3 \times 10^6$ | 0 (UNTREATED CONTROL) |
| | 10 min. | 0.1% | 0 | 100% |

Actual inactivation times may have been shorter than reported in the table. These data indicate that the core composition of the present invention is an effective topical disinfectant.

EXAMPLE X

Anti-microbial Activity of Core Composition

In a second experiment to test the anti-microbial activity of the four acid core composition of the present invention, the core composition was prepared in accordance with the method of Example II, above and tested in various concentrations for activity against bacteria. The core composition was prepared in several dilutions in sterile water and each preparation was inoculated with *C. albicans, P. aeruginosa,* and *S. aureus.* Each inoculated dilution was allowed to sit for 10 mins. and the bacteria and fungi were removed and put into Letheen broth. The bacteria demonstrated a Log 6 kill with the 20% dilution. The fungus demonstrated less than a Log 4 kill at 65% dilution. Additionally, *C. albicans* was subjected to a 20% dilution of the core composition for 1, 2, 3, 4, and 5 hours; Log kill was less than Log 4 at 5 hours.

EXAMPLE XI

Water Treatment

One gallon of the core composition prepared as described in Example II, above, was mixed with one gallon of distilled water. About 20 weight percent of that volume was removed from the water before addition to the core composition and replaced with the equivalent weight of copper sulfate pentahydrate. Dilutions of the resulting solution were prepared at 1:30,000, 1:60,000, 1:120,000, 1:240,000, and 1:480,000 using sterile water, and each dilution was inoculated with $10^8$ organisms *Vibrio cholera* at the time points 0, 20 mins., 2 hrs., 5 hrs., 10 hrs., 24 hrs., and 48 hrs. One milliliter was removed and put into neutralizing letheen broth, incubated for seven days, and observed for growth. All tubes showed no growth at or after the 2 hr. exposure.

EXAMPLE XII

Preparation of Topical Disinfectant

The core composition of Example II, above was diluted by mixing equal parts of that composition with water. When applied to the skin, food (especially vegetables and fruits), and plastic (such as the mouth-piece of a telephone handset), glass, metal, and/or ceramic surfaces, the resulting composition is an effective topical disinfectant.

EXAMPLE XIII

Battery Fluid Replacement

When three parts (by weight) of the core composition of Example II, above, are added to one part sulfuric acid, the resulting aqueous acid is used as an additive or replacement for battery acid.

EXAMPLE XIV

Treatment of Infection

Protein A purchased as a dry powder from a commercial source is overcoated with EUDRAGITS acrylate polymer (Rohm-Tech, Malden, Mass.) dissolved in organic solvents for application using an Air Suspension Coater (Coatings Place, Verona, Wis.). The particular grade of EUDRAGITS polymer selected is a polymer which dissolves at a pH of about 5.0–5.5. The microencapsulated protein A is mixed with the inert bioadhesive CARBOPOL (B.F. Goodrich Co., Cleveland, Ohio) and the core composition of Example II in approximately equal parts (by weight). The resulting acidic suspension of encapsulated protein A is sprayed, using a conventional aerosal pump spray bottle, onto bacterially-induced skin infections and allowed to air dry, the adhesive both causing adherence of the microcapsules and forming a film-like "dressing" on the infected area. The initial low pH of the suspension is bacteriostatic, and as the amount of acid is diluted and available protons in the aqueous formulation are donated to available biomolecules, the pH in the area of the infection gradually rises to the point at which the microcapsules break down and the protein A is released to stimulate the immune system so as to increase the localized immune response to the causative agent.

Although described in terms of the preferred embodiments and the examples set out above, it will be recognized by those skilled in the art that certain changes may be made to these specific embodiments without departing from the manner in which the components thereof function to achieve their intended results(s). There are, for instance, many organic acids which, although not specifically listed above in the interest of brevity (and also because the patent laws require illustration and exemplification, and not the listing of every possible combination) which are expected on the basis of their molecular structure to perform quite adequately as the third and fourth acids of the four acid core composition of the present invention. Likewise, the four acid core composition of the present invention is formulated into a number of aqueous agents not specifically listed herein for use in a number of ways not listed, but which are contemplated by the present invention. Again, it simply is not practical to list every possible combination and method of use. In short, the scope of the present invention is as set out in the following claims.

What is claimed is:

1. An aqueous acidic composition consisting essentially of first and second inorganic acids, said first acid being a strong acid which dissociates essentially completely in water and said second acid being selected from the group consisting of inorganic acids having a dissociation constant of less than about $10^{-1}$;

third and fourth acids, said third acid being selected from the group consisting of organic acids having a dissociation constant of from about $10^{-1}$ to about $10^{-5}$ and said fourth acid being selected from the group consisting of organic acids having a dissociation constant of less than about $10^{-4}$; and water, said first and second acids each comprising between about 5 and about 20 weight percent of the final composition and said third and fourth acids each comprising between about 1 and about 5 weight percent of the final composition.

2. The composition of claim 1 wherein said third acid is selected from the group consisting of hydroxy- and alpha-hydroxycarboxylic acids.

3. The composition of claim 1 wherein said fourth acid is a dicarboxylic acid.

4. The composition of claim 1 wherein the dissociation constant of said third acid is between about $10^{-1}$ and about $10^{-3}$.

5. The composition of claim 4 wherein the dissociation constant of said fourth acid is less than about $10^{-4}$.

6. A pharmaceutical agent including the composition of claim 1.

* * * * *